(12) United States Patent
Katoh et al.

(10) Patent No.: US 9,283,034 B2
(45) Date of Patent: Mar. 15, 2016

(54) RECANALIZATION SYSTEM USING RADIOFREQUENCY ENERGY

(75) Inventors: Osamu Katoh, Nagoya (JP); Wayne Ogata, San Ramon, CA (US)

(73) Assignee: RetroVascular, Inc., Pleasanton, CA (US)

( * ) Notice: Subject to any disclaimer, the term of this patent is extended or adjusted under 35 U.S.C. 154(b) by 822 days.

(21) Appl. No.: 12/753,844

(22) Filed: Apr. 2, 2010

(65) Prior Publication Data

US 2010/0256616 A1    Oct. 7, 2010

Related U.S. Application Data

(63) Continuation-in-part of application No. 12/680,500, filed as application No. PCT/US2008/077403 on Sep. 23, 2008, now Pat. No. 8,911,435.

(60) Provisional application No. 60/975,473, filed on Sep. 26, 2007, provisional application No. 61/298,547, filed on Jan. 26, 2010.

(51) Int. Cl.
*A61B 18/18* (2006.01)
*A61B 18/14* (2006.01)
(Continued)

(52) U.S. Cl.
CPC .............. *A61B 18/18* (2013.01); *A61B 5/0059* (2013.01); *A61B 8/12* (2013.01); *A61B 18/1492* (2013.01); *A61M 5/00* (2013.01); *A61M 13/003* (2013.01); *A61B 18/1815* (2013.01); *A61B 18/24* (2013.01); *A61B 2018/0041* (2013.01); *A61B 2018/1861* (2013.01); *A61B 2019/5276* (2013.01); *A61N 7/022* (2013.01)

(58) Field of Classification Search
CPC .......... A61B 18/18; A61B 18/12; A61B 8/12; A61B 18/24; A61B 18/1492; A61B 2018/0041; A61B 2018/1861; A61B 2019/5276
USPC ....................................................... 606/32–52
See application file for complete search history.

(56) References Cited

U.S. PATENT DOCUMENTS 5,041,109 A    8/1991 Abela
5,366,443 A    11/1994 Eggers et al.
(Continued)

FOREIGN PATENT DOCUMENTS

WO    9713471 A1    4/1997
WO    0009020    2/2000
(Continued)

OTHER PUBLICATIONS

International Search Report and Written Opinion in International Application No. PCT/US2007/003706, dated Sep. 22, 2008.
(Continued)

*Primary Examiner* — Aaron Roane
(74) *Attorney, Agent, or Firm* — LeClairRyan, a Professional Corporation (57) ABSTRACT

A method and systems for treating chronic total occlusions, particularly those that are difficult to treat, is disclosed. In this approach, recanalizing the CTO is achieved using a combined antegrade and retrograde approach. The proximal end of the occlusion is penetrated using an antegrade wire, using a traditional approach. Using collateral vessels, the distal end of the occlusion is crossed in a retrograde fashion. By appropriately maneuvering each member and applying radiofrequency energy between the proximal and distal ends of the occlusion, a continuous channel is created.

47 Claims, 9 Drawing Sheets

(51) Int. Cl.

| | |
|---|---|
| A61B 5/00 | (2006.01) |
| A61B 8/12 | (2006.01) |
| A61M 5/00 | (2006.01) |
| A61M 13/00 | (2006.01) |
| A61B 18/24 | (2006.01) |
| A61B 18/00 | (2006.01) |
| A61B 19/00 | (2006.01) |
| A61N 7/02 | (2006.01) |

(56) References Cited

U.S. PATENT DOCUMENTS

| | | | |
|---|---|---|---|
| 5,419,767 A | 5/1995 | Eggers et al. | |
| 5,429,131 A * | 7/1995 | Scheinman | A61N 1/0587 600/374 |
| 5,501,694 A | 3/1996 | Ressemann et al. | |
| 5,514,128 A | 5/1996 | Hillsman et al. | |
| 5,695,517 A | 12/1997 | Marin et al. | |
| 5,895,398 A | 4/1999 | Wensel et al. | |
| 6,068,645 A * | 5/2000 | Tu | 606/200 |
| 6,235,044 B1 * | 5/2001 | Root et al. | 606/200 |
| 6,416,523 B1 | 7/2002 | Lafontaine | |
| 6,454,775 B1 | 9/2002 | Demarais et al. | |
| 6,911,026 B1 | 6/2005 | Hall et al. | |
| 6,936,056 B2 | 8/2005 | Nash et al. | |
| 7,037,316 B2 | 5/2006 | McGuckin et al. | |
| 2002/0052602 A1 * | 5/2002 | Wang | A61B 18/1445 606/41 |
| 2003/0028200 A1 | 2/2003 | Berg et al. | |
| 2004/0082962 A1 | 4/2004 | Demarais et al. | |
| 2004/0230219 A1 | 11/2004 | Roucher, Jr. | |
| 2005/0154400 A1 | 7/2005 | Kato et al. | |
| 2005/0171478 A1 | 8/2005 | Selmon et al. | |
| 2005/0251134 A1 | 11/2005 | Woloszko et al. | |
| 2006/0079880 A1 | 4/2006 | Sage et al. | |
| 2006/0224112 A1 | 10/2006 | Lentz | |
| 2007/0043389 A1 | 2/2007 | Shindelman | |
| 2007/0049867 A1 | 3/2007 | Shindelman | |
| 2007/0112342 A1 | 5/2007 | Pearson et al. | |
| 2007/0208368 A1 | 9/2007 | Katoh et al. | |
| 2008/0039935 A1 | 2/2008 | Buch et al. | |
| 2008/0306499 A1 | 12/2008 | Katoh et al. | |
| 2009/0192508 A1 * | 7/2009 | Laufer et al. | 606/41 |
| 2010/0292685 A1 | 11/2010 | Katoh et al. | |

FOREIGN PATENT DOCUMENTS

| | | | |
|---|---|---|---|
| WO | 2009/042614 A1 | 4/2009 | |
| WO | 2009042614 A1 | 4/2009 | |

OTHER PUBLICATIONS

International Search Report and Written Opinion in International Application No. PCT/US2008/077403, dated Dec. 1, 2008.
International Search Report and Written Opinion in International Application No. PCT/US2009/041287, dated Jul. 7, 2009.
Office Action in U.S. Appl. No. 12/150,111, mailed Nov. 18, 2010.
Office Action in U.S. Appl. No. 11/706,041, mailed May 12, 2010.
Notice of Allowance in U.S. Appl. No. 11/706,041, mailed Nov. 26, 2010.
Office Action in U.S. Appl. No. 12/150,111, mailed Apr. 22, 2011.
Canadian Office Action in Canadian Application No. 2,641,729, dated May 14, 2010.
Australian Office Action in Australian Application No. 2007215224, dated Apr. 8, 2010.
Bourassa, Martial G. et al., "Bypass Angioplasty Revascularization Investigation: Patient Screening, Selection, and Recruitment," The American Journal of Cardiology, vol. 75, Issue 9, pp. 3C-8C, 1995.
Colombo, Antonio et al., "Treating Chronic Total Occlusions Using Subintimal Tracking and Reentry: The STAR Technique," Catheterization and Cardiovascular Interventions, vol. 64, No. 4, pp. 407-411, 2005.
Ito, Shigenori et al., "Novel Technique Using Intravascular Ultrasound-Guided Guidewire Cross in Coronary Intervention for Uncrossable Chronic Total Occlusions," Circulation Journal, vol. 68, No. 11, pp. 1088-1092, Nov. 2004.
Kimura, Bruce J. et al., "Subintimal Wire Position During Angioplasty of a Chronic Total Coronary Occlusion: Detection and Subsequent Procedural Guidance by Intravascular Ultrasound," Catheterization and Cardiovascular Diagnosis, vol. 35, No. 3, pp. 262-265, 1995.
King, Spencer B. et al., "A Randomized Trial Comparing Coronary Angioplasty with Coronary Bypass Surgery," The New England Journal of Medicine, vol. 331, No. 16, pp. 1044-1050, Oct. 20, 1994.
Kinoshita, Isao et al., "Coronary Angioplasty of Chronic Total Occlusions With Bridging Collateral Vessels: Immediate and Follow-Up Outcome From a Large Single-Center Experience," Journal of the American College of Cardiology, vol. 26, No. 2, pp. 409-415, Aug. 1995.
Matsubara, Tetsuo et al., "IVUS-Guided Wiring Technique: Promising Approach for the Chronic Total Occlusion," Catheterization and Cardiovascular Interventions, vol. 61, No. 3, pp. 381-386, 2004.
Melchior, Jean-Paul et al., "Improvement of Left Ventricular Contraction and Relaxation Synchronism After Recanalization of Chronic Total Coronary Occlusion by Angioplasty," Journal of the American College of Cardiology, vol. 9, No. 4, pp. 763-768, Apr. 1987.
Olivari, Zoran et al., "Immediate Results and One-Year Clinical Outcome After Percutaneous Coronary Interventions in Chronic Total Occlusions: Data From a Multicenter, Prospective, Observational Study (TOAST-GISE)," Journal of the American College of Cardiology, vol. 41, No. 10, pp. 1672-1678, 2003.
Suero, James A. et al., "Procedural Outcomes and Long-Term Survival Among Patients Undergoing Percutaneous Coronary Intervention of a Chronic Total Occlusion in Native Coronary Arteries: A 20-Year Experience," Journal of the American College of Cardiology, vol. 38, No. 2, pp. 409-414, 2001.
Bolia, A. et al. "Recanalization of Iliac Artery Occlusion by Subintimal Dissection Using the Ipsilateral and the Contralateral Approach," Clinical Radiology, vol. 52, pp. 684-687, 1997.
Spinosa, David J. et al. "Simultaneous Antegrade and Retrograde Access for Subintimal Recanalization of Peripheral Arterial Occlusion," Journal of Vascular and Interventional Radiology, vol. 14, Issue 11, pp. 1449-1454, Nov. 2003.
Australian Office Action in Australian Application No. 2008304599, dated Feb. 22, 2011.
Korean Non-Final Rejection for Korean Application No. 10-2008-7022167, dated Nov. 23, 2010.
Australian Examination Report issued on Australian Patent Application No. 208304599, dated Feb. 22, 2011.
Filed Response dated Jul. 20, 2012 to Feb. 22, 2011 Examination Report issued by Australian Patent Office issued for Patent Application Serial No. 208304599.
Australian Examination Report issued on Australian Application No. 208304599, dated Sep. 4, 2012.
Filed Response dated Oct. 11, 2012 to Sep. 4, 2012 Second Examination Report issued by Australian Patent Office on Patent Application Serial No. 208304599.
Extended Supplementary European Search Report dated Jul. 24, 2012, Issued by the European Patent Office on Jul. 24, 2012, Issued by the European Patent Office for European patent application serial No. 08834456.9.
Filed Response dated Nov. 19, 2012 to Extended Supplementary European Search Report dated Jul. 24, 2012, Issued by the European Patent Office for European patent application serial No. 08834456.9.
Extended European Search Report for European Patent Application No. 11763547.4 (Aug. 8, 2013).

* cited by examiner

RECANALIZATION SYSTEM USING RADIOFREQUENCY ENERGY

CROSS-REFERENCES TO RELATED APPLICATIONS

This application is a continuation-in-part of U.S. patent application Ser. No. 12/680,500, a national stage application under 35 U.S.C. §371, now issued as U.S. Pat. No. 8,911,435, filed Mar. 26, 2010, titled "Recanalizing Occluded Vessels Using Radio Frequency Energy", which claims priority from PCT Application No. PCT/US2008/077403, filed Sep. 23, 2008, which claims the priority benefit of U.S. Provisional Application No. 60/975,473, filed Sep. 27, 2007. This application also claims priority to U.S. Provisional Application Ser. No. 61/298,547, filed on Jan. 26, 2010, titled "Recanalizing Occluded Vessels Using Radiofrequency Energy".

FIELD OF THE INVENTION

This invention relates generally to dealing with occlusions of the lumen and more specifically to apparatus and methods for crossing severe or total chronic occlusions of lumens in the body using radiofrequency energy.

DESCRIPTION OF THE RELATED ART

Chronic total occlusion (CTO) is the complete blockage of a vessel and may have serious consequences if not treated in a timely fashion. The blockage could be due to atheromatous plaque or old thrombus. One of the common procedures for treating CTOs of the coronary arteries is percutaneous transluminal coronary angioplasty (PTCA). During a PTCA procedure, a small incision is typically made in the groin. A guiding catheter over a guidewire is introduced into the femoral artery and advanced to the occlusion. At times, with gentle maneuvering, the guidewire is able to cross the occlusion. A balloon-tipped angioplasty catheter is then advanced over the guidewire to the occlusion. The balloon is inflated, separating or fracturing the atheroma. Often times, a stent is subsequently or simultaneously deployed. Some of the common steps involved in the PTCA procedure for CTOs are the simultaneous injection of a contrast agent in the contra-lateral vessel, securing backup force or stabilization for a guidewire (which could invoke additional personnel to handle the catheter), puncturing the plaque, drilling or rotating the guidewire to push it through the dense plaque, etc. Because of the stiff resistance sometimes offered by dense plaque, one could be forced to use stiff wires. Occasionally, the wires could puncture the vessel wall calling for remedial measures.

The most common percutaneous coronary intervention (PCI) failure mode for CTOs is inability to successfully pass a guidewire across the lesion into the true lumen of the distal vessel. To date, there is no consensus on how best to treat CTO after attempts with conventional guidewires have failed. Different strategies for CTOs have been developed including the side branch technique, the parallel wire technique, and the IVUS guided technique. Mechanical and energy based devices have also been proposed for passing guidewires through hard calcified occlusions, such as mechanical cutting or oscillation and laser or ultrasound or radiofrequency (RF) energy ablation. Each of these devices works by strictly utilizing an antegrade approach and locally applying energy (typically in the form of heat) at the tip of the guidewire or catheter device in order to create a channel and hopefully enter the distal true lumen.

RF energy is widely used to coagulate, cut or ablate tissue. In both modalities, monopolar and bipolar, conductive electrodes contact the tissue to be treated. In the monopolar mode, the active electrode is placed in contact with the tissue to be treated and a return electrode with a large surface area is located on the patient at a distance from the active electrode. In the bipolar mode, the active and return electrodes are in close proximity to each other bracketing the tissue to be treated. Sometimes an array of electrodes is used to provide better control over the depth of penetration of the RF field and hence control over the temperatures to which the tissue is heated. There are many disadvantages with each mode. For example, in the monopolar arrangement, because of the large physical separation between the electrodes there are frequent reports of local burning at the electrode sites. This would clearly be undesirable where one of the electrodes will be inside a blood vessel. The other serious issue is the likelihood of forming blood clots. The tissue that is in contact with the electrodes can be coagulated or ablated. In the case of the electrodes being present inside a blood vessel, the formation of dangerous blood clots would obviously be undesireable.

In an attempt to overcome the issues described above, various device and electrode configurations are described in the following patents. U.S. Pat. Nos. 5,366,443 and 5,419,767 describe the use of RF electrodes on a catheter to cross a lesion. These patents describe a bipolar electrode assembly at the distal tip of a catheter that is in contact with the occlusion, and patentees claim that application of RF energy ablates the occlusion and renders the occlusion susceptible for the guidewire to penetrate. This method has the drawback that careful tracking of the occlusion and the ablation process is necessary to avoid trauma to the vessel walls or healthy tissue, since the possibility of short-circuiting of current through healthy tissue instead of the occlusion is high. U.S. Pat. No. 5,419,767 overcomes this limitation to a certain extent through the use of a multiple electrode array. However, this device requires a channel to be pre-created through the occlusion so that the device can be passed through a guidewire traversing this channel, which is not always easy.

U.S. Pat. No. 5,514,128 to Hillsman et al. describes a laser catheter device that enables ablation of an occlusion in the vasculature. This system has similar drawbacks to the ones described above-need for a guidance system, potential for healthy tissue to be ablated, complexity (and hence cost) of the device, etc.

One major problem with the existing devices is the potential for the ablation energy to damage the walls of the vasculature, in the absence of a mechanism to track the orientation and position of the energy delivery member. Several devices exist in the prior art that address the issue of tracking and steering of the energy delivery element. U.S. Pat. No. 6,911,026 to Hall et al. describes a magnetic steering and guidance system to direct an ablation device that delivers RF energy at the tip in a unipolar configuration where the return electrode is placed externally in contact with the body or in a bipolar configuration where the return electrode is a ring surrounding the central wire electrode.

U.S. Pat. No. 6,416,523 to Lafontaine discusses a mechanical cutting device where the guidance is provided by measuring impedance of the tissue in contact. The guidance system senses the difference in impedance between the stenotic tissue and the vessel wall and directs the cutting element to the occlusion.

However, none of these alternate strategies have provided satisfactory results for the most challenging of the CTOs. In case of hard calcified occlusions, the revascularization procedure can be tedious and time consuming. Therefore, there is a need for improved methods of ablating or disrupting the occlusive material that are safe, efficacious and fast. It would be beneficial to have alternate techniques and devices that would recanalize a CTO without the shortcomings of the current techniques.

CTOs that are hard to recanalize, either because of the tortuous anatomy of the diseased vessel, or because the proximal end of the stenosis is too hard for the guide wire to penetrate, or other characteristics of the CTO that would make the standard procedure vulnerable to failure would benefit from newer approaches to recanalize CTOs. Recently a combined antegrade-retrograde approach has been proposed for recanalizing chronic occlusions (U.S. application Ser. No. 11/706,041). The method disclosed in the co-pending application would benefit from the use of energy for crossing CTOs.

SUMMARY OF THE INVENTION

Various methods and devices are provided to overcome some of the commonly encountered problems in treating chronic total occlusions. One aspect of this invention is to provide a method and systems for successfully recanalizing an occluded vessel by advancing, in combination, guidewires in an antegrade and retrograde fashion to the occlusion and applying RF energy between the proximal and distal ends of the occlusion. The RF energy application across the occlusion is accomplished using a bipolar arrangement, where one electrode is located on the antegrade guidewire and the other electrode that makes up the bipolar arrangement is located on the retrograde guidewire. In one aspect, the present invention discloses a method of recanalizing an occluded vessel comprising advancing in an antegrade fashion a first longitudinal member through a proximal end of an occlusion, advancing in a retrograde fashion a second longitudinal member through a distal end of the occlusion, applying RF energy between the distal ends of the antegrade and retrograde guidewires, ablating the tissue locally, and creating a channel through which a guidewire could be advanced. In another embodiment, the retrograde guidewire could have a deployable capture mechanism at its distal end and upon deployment could snare the antegrade guidewire.

In another aspect, this invention relates to a catheter assembly for recanalizing an occluded vessel comprising an antegrade longitudinal member with a distal end containing an RF electrode and a retrograde longitudinal member with a distal end containing a second RF electrode; and the proximal end of the catheter assembly connected to an RF generator. Additionally, a temperature measuring element could be disposed on the distal ends of the antegrade or retrograde longitudinal member. The RF generator could also be programmed to treat the tissue for a pre-set time or until a set condition has been reached. One such condition could be till the occlusion has reached a pre-determined temperature. Another condition could be the impedance of the occlusion.

In another aspect, the invention is a kit for recanalizing occluded vessels comprising one or more of the following: an antegrade guidewire, a retrograde guidewire, a dilating device, a capture device and an injection catheter, wherein at least one of these devices contains at least one electrode. Additionally, the proximal ends of this device are configured to be coupled with an RF generator.

Other aspects of the invention include methods corresponding to the devices and systems described above.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE PREFERRED EMBODIMENTS

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

The present embodiments combine the use of RF energy delivered through antegrade and retrograde members for recanalizing occluded lumens, particularly chronic total occlusions. The methods and systems described herein recanalize difficult to cross occlusions by taking advantage of an antegrade and retrograde approach to establish a bipolar electrode arrangement across the occlusion. This approach minimizes the potential of the vessel wall becoming perforated or injured, as may otherwise occur in a conventional bipolar RF treatment approach, where both RF electrodes are on the same side of the occlusion. Because the electrodes are distributed on opposite sides of the occlusion, the tissue that is ablated by the RF treatment (i.e., the occlusion) is well contained between the electrodes. This also allows the user to localize the treatment to the occlusion.

As disclosed in the co-pending U.S. patent application Ser. No. 11/706,041 by the same inventors, which is incorporated herein in its entirety, in the controlled antegrade and retrograde tracking (CART) technique the retrograde approach takes advantage of an intercoronary channel. Such a channel may be an epicardial channel, an inter-atrial channel, an intraseptal channel (also referred to as septal collateral), or a bypass graft. The basic concept of the CART technique is to create a channel through an occlusion, preferably with limited dissections, by approaching the occlusion both antegradely and retrogradely.

While the combined antegrade and retrograde approach has been effective in crossing difficult to cross lesions, it has been observed that using energy, for example RF energy, to ablate or alter the tissue in a controlled fashion is beneficial in crossing hard to cross lesions. Such controlled energy deployment is achieved using a bipolar arrangement of the electrodes, where one electrode is located on the antegrade element and the other electrode that constitutes the bipolar arrangement is located on the retrograde element. These electrodes can also be referred to as the return and active electrodes. They are also referred to as the anode and cathode, respectively. The electrodes could also be arranged in an array (multiple electrodes), where the electrode arrangement provides better control over the depth of penetration of the RF field and thereby provides the ability to control the tissue temperature.

Figure 1:
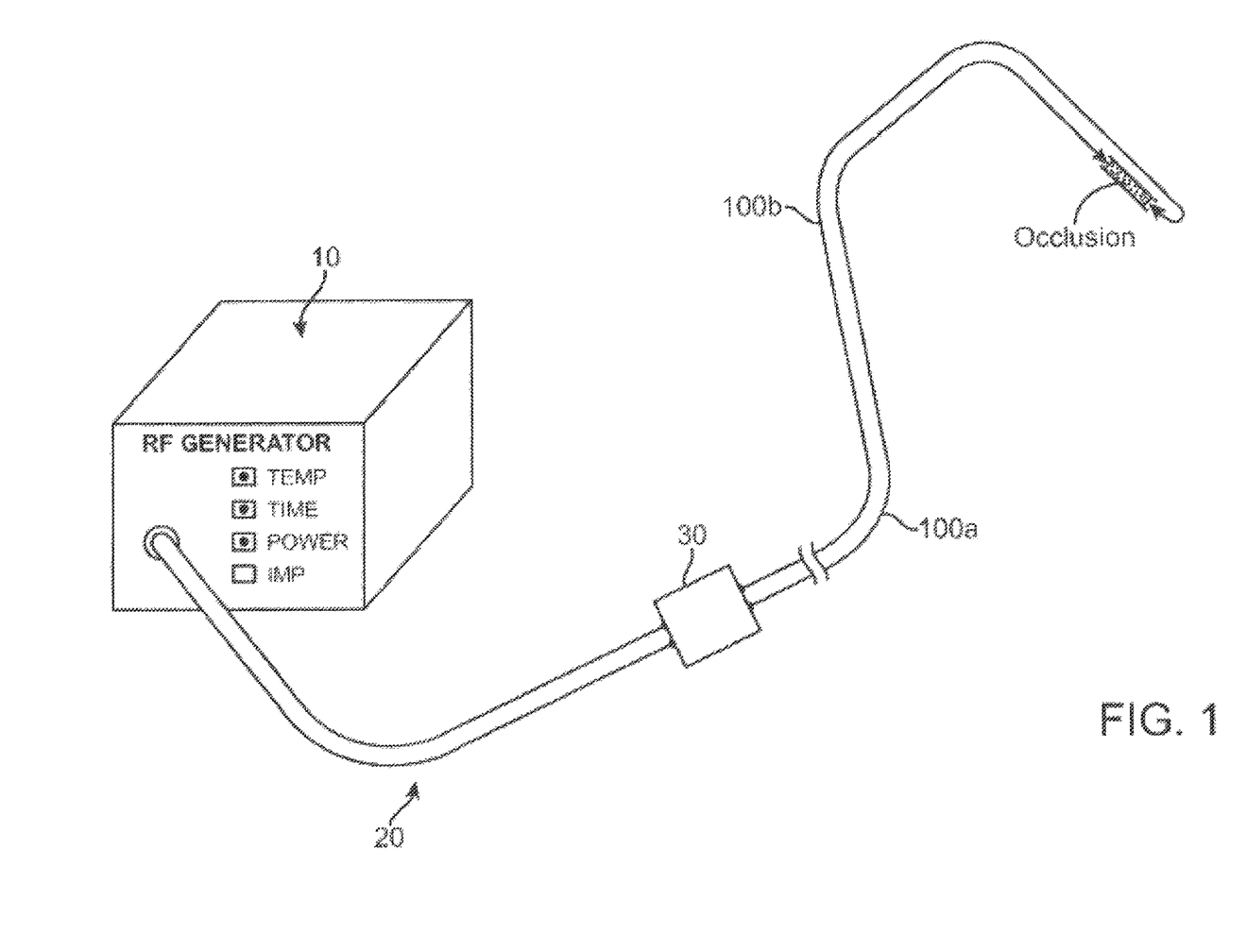
FIG. 1 is a schematic showing an RF generator connected to the longitudinal members.

FIG. 1 shows a system for recanalizing occluded vessels using RF energy. The system comprises longitudinal members 100a and 100b for delivering RF energy to an occlusion. As indicated in FIG. 1, longitudinal member 100a serves as an antegrade member and longitudinal member 100b serves as a retrograde member. An RF generator 10 (also referred to as a controller) serves as the source of RF energy to be provided to longitudinal members 100a and 100b. Optionally, the RF generator may be a hand-held battery-operated device. Longitudinal members 100a and 100b may be guidewires, catheters, micro-catheters, or dilating catheters. In a preferred embodiment, longitudinal members 100a and 100b are guidewires. Thus, while in the following description the term "guidewire" is used to refer to a longitudinal member 100a or 100b, it is understood that the term "guidewire" as used herein is intended to include any other type of longitudinal member.

To provide RF energy from the RF generator 10 to the guidewires 100a and 100b, a pigtail 20 connects at its proximal end to the RF generator 10 and terminates at its distal end in a connector 30. Connector 30 is a standard connector that couples the input and output signals of the RF generator 10 to the guidewires 100a and 100b.

One embodiment of the connector would be a locking tool or torque device which can be placed over the guidewire. In such a configuration, the locking tool or torque device is configured to make electrical contact with a portion of the guidewire (such as the guidewire corewire) that conducts radiofrequency energy to, or from, the one or more electrodes disposed on the guidewire. In such a configuration, the locking tool or torque device would also be configured to connect to a radiofrequency generator, thereby electrically connecting the generator to the guidewire and electrodes. Means of locking the connector to the guidewire may include compressible prongs, screws, sliding rings, or other mechanisms commonly utilized in torque devices.

Guidewires 100a and 100b are configured to have sufficient torsional rigidity and longitudinal flexibility to advance through an occlusion, and to align their electrodes in a direction away from the vessel wall, towards the other longitudinal member, or any combination thereof.

Figure 2:
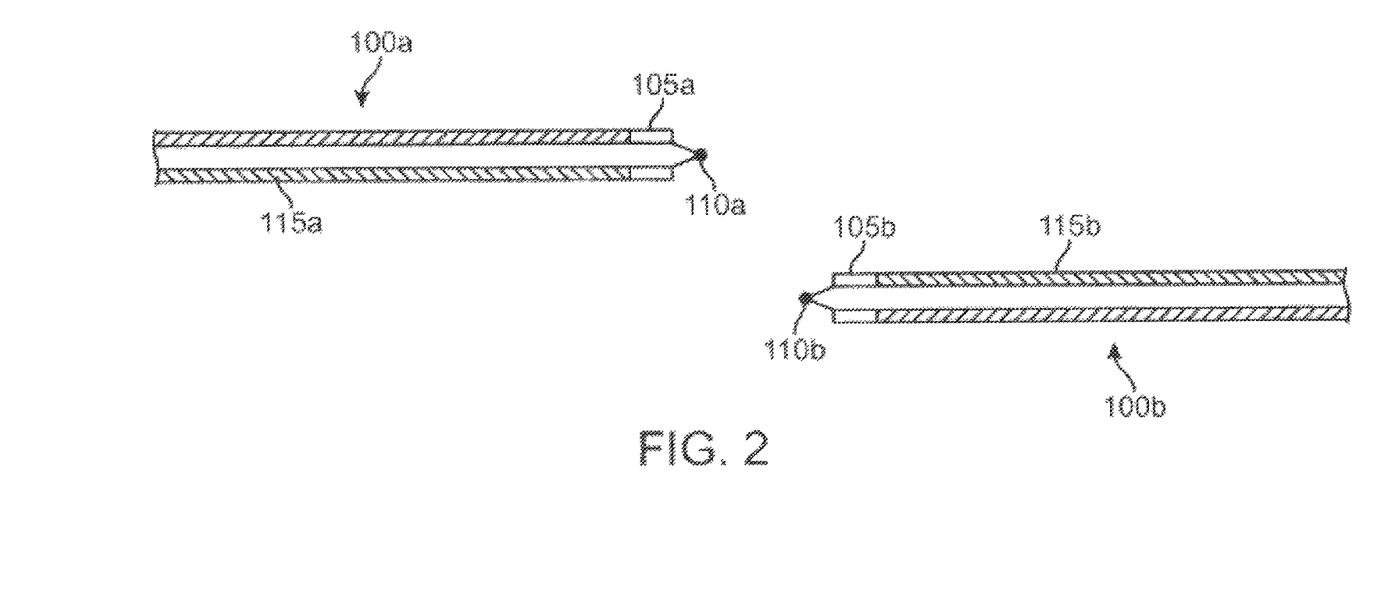
FIG. 2 shows the features of the longitudinal members.

As shown in FIG. 2, the antegrade and retrograde guidewires 100a and 100b have conductive electrodes 105a and 105b, respectively, at their distal ends. In one embodiment, the electrodes 105a and 105b are located on one side of their respective guidewires 100a and 100b, thereby providing the operating physician with the freedom to allow the electrode-free side of the guidewire to touch the vessel wall (if needed) while still directing the RF energy away from the vessel wall. Additionally, this allows the configuration to direct the RF energy away from the vessel wall, thereby minimizing potential RF injury to the vessel wall. In one embodiment, one or more of the guidewires comprises a plurality of electrodes arranged in an array.

Conductive wires (not shown) connect the electrodes 105a and 105b to connector 30 to deliver RF energy from the RF generator 10 to the electrodes 105a and 105. The exterior of the guidewires are covered by non-conductive layers 115a and 115b, respectively, that sandwich the conductive wires between the guidewires and the non-conductive layers. In one embodiment, the non-conductive layers 115a and 115b comprise a sheath or a coating. Example of materials may include Teflon, ceramic, polyimide, parylene, or other suitable materials. Examples of methods which could be employed for coating may include spraying, dipping, vapor deposition, or plasma deposition.

Figure 2A:
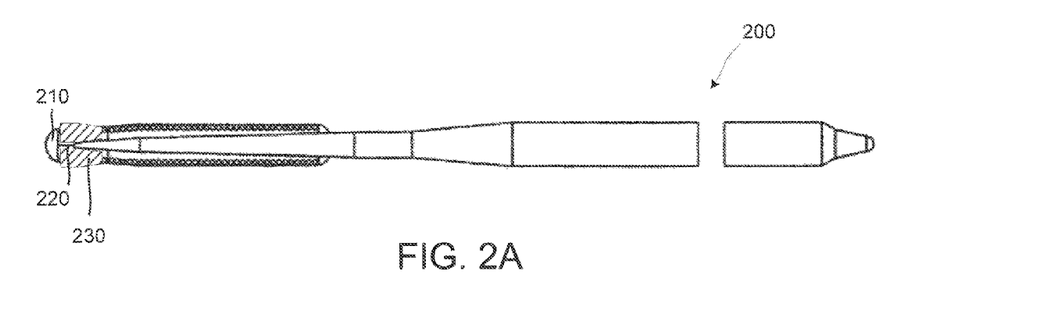
FIGS. 2A-2B show various embodiments of longitudinal members comprising insulators.

In another embodiment, the conductive wires are insulated by using a heat resistant material on the guidewire to protect the device and surrounding tissue from excessive heat. FIG. 2A shows a cross-sectional view of a guidewire comprising an electrode and an insulator, in accordance with an embodiment of the present invention. A guidewire 200 comprises an electrode 210 as its distal tip. The electrode 210 is electrically coupled to the guidewire's corewire via an electrically conductive ribbon 220 or other such electrically conductive connector. An insulator 230 is disposed at a distal portion of the guidewire 200 to deflect some of the heat that is generated when the electrode 210 is energized with radiofrequency energy, thereby protecting the rest of the device from such heat. The insulator 230 may wrap around the distal portion of the guidewire 200, as shown in FIG. 2A, or it may be configured as a plurality of discrete pieces disposed at the distal portion of the guidewire 200. The insulator may or may not directly contact electrodes.

Figure 2B:
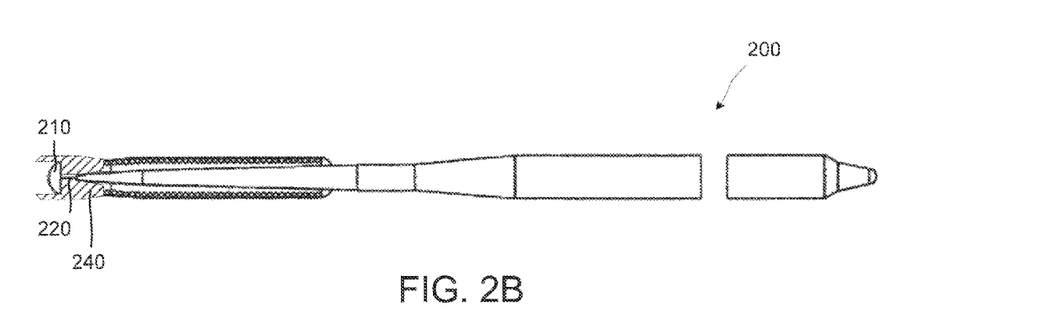

In another embodiment, the insulator may be configured to protrude forward so that the electrode is recessed. An example of this is shown in FIG. 2B, showing a protruding insulator 240 configured to extend beyond the electrode 210, thereby recessing the electrode 210. This limits the exposure of the electrode 210 to surrounding tissue, while leaving the electrode sufficiently exposed to create the bipolar arrangement.

In one embodiment, and as further shown in FIG. 2, the guidewires 100a and 100b comprise temperature measuring elements 110a and 110b at the distal tip of the antegrade and retrograde guidewires, respectively. In one embodiment, the temperature measuring elements 110a and 110b comprise thermocouples or thermistors that are connected to the connector 30. In another embodiment, pressure measuring elements are placed on the distal ends of the guidewires to detect a change in pressure upon activation of the RF energy.

RF generator 10 is configured to allow the user to set a maximum temperature, a treatment time period, a level of RF power, or a combination of these control parameters. The treatment time period indicates the period of time over which the RF energy will flow between the electrodes. The maximum temperature setting serves as a threshold temperature for the tissue that is in contact with the electrodes, and the RF generator 10 can be set to reduce or shut off power to one or both electrodes when one or more of the temperature measuring elements 110a and 110b indicate a tissue temperature at or near the threshold.

In one embodiment, the generator 10 is capable of measuring the impedance of the tissue between the two electrodes 105a and 105b. Based on the type of the occlusion (i.e., the nature of the calcified material), the user can choose the appropriate combination of temperature, treatment time, and the amount of RF energy to be provided to the tissue to achieve a safe and effective treatment. Alternatively, the treatment may proceed with the user manually controlling the parameters during the recanalization procedure, with the user treating the occlusion until recanalization is achieved.

Figure 3A:
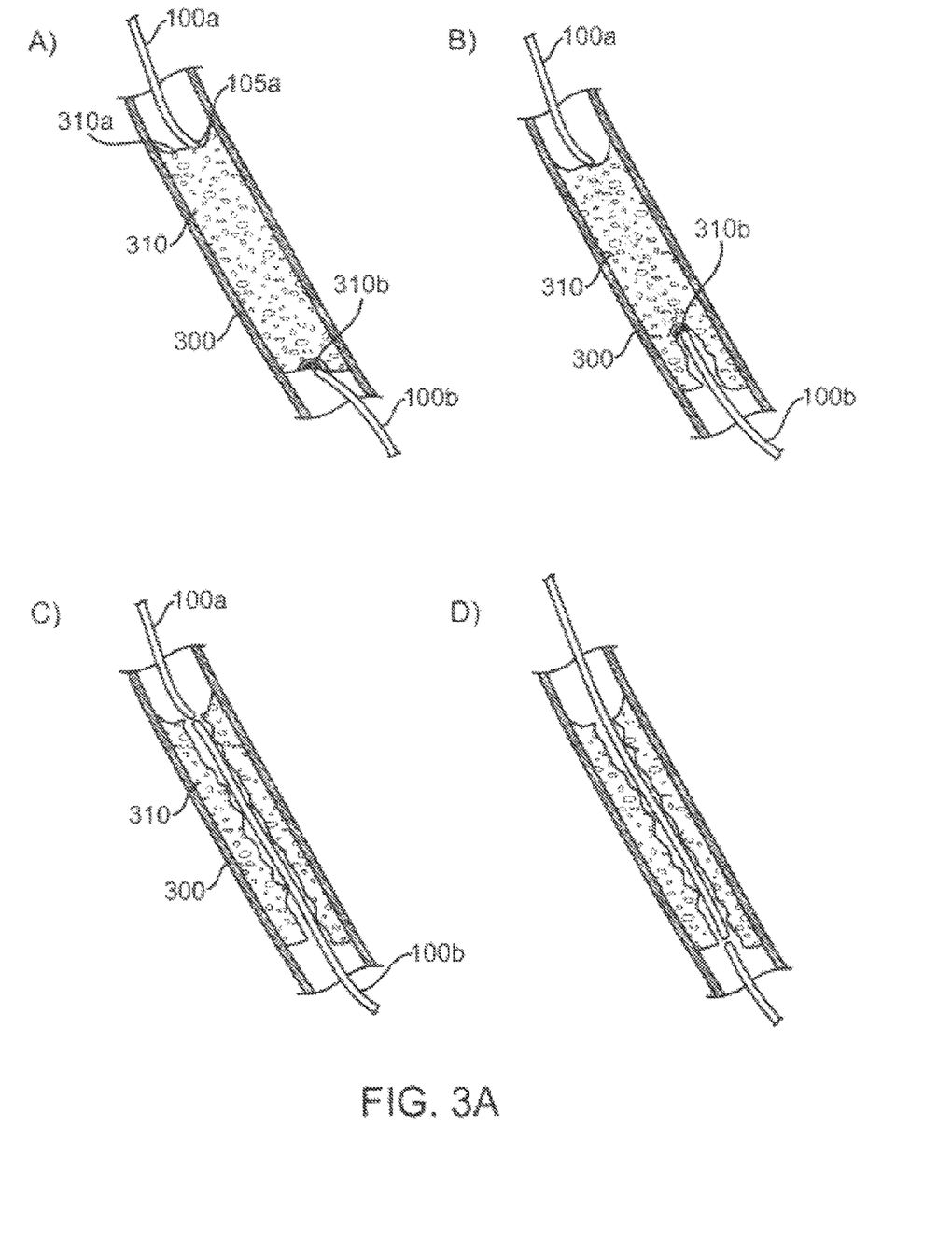
FIGS. 3A and 3B show the steps involved in recanalizing a CTO using bipolar RF and combined antegrade and retrograde approach.
Figure 3B:
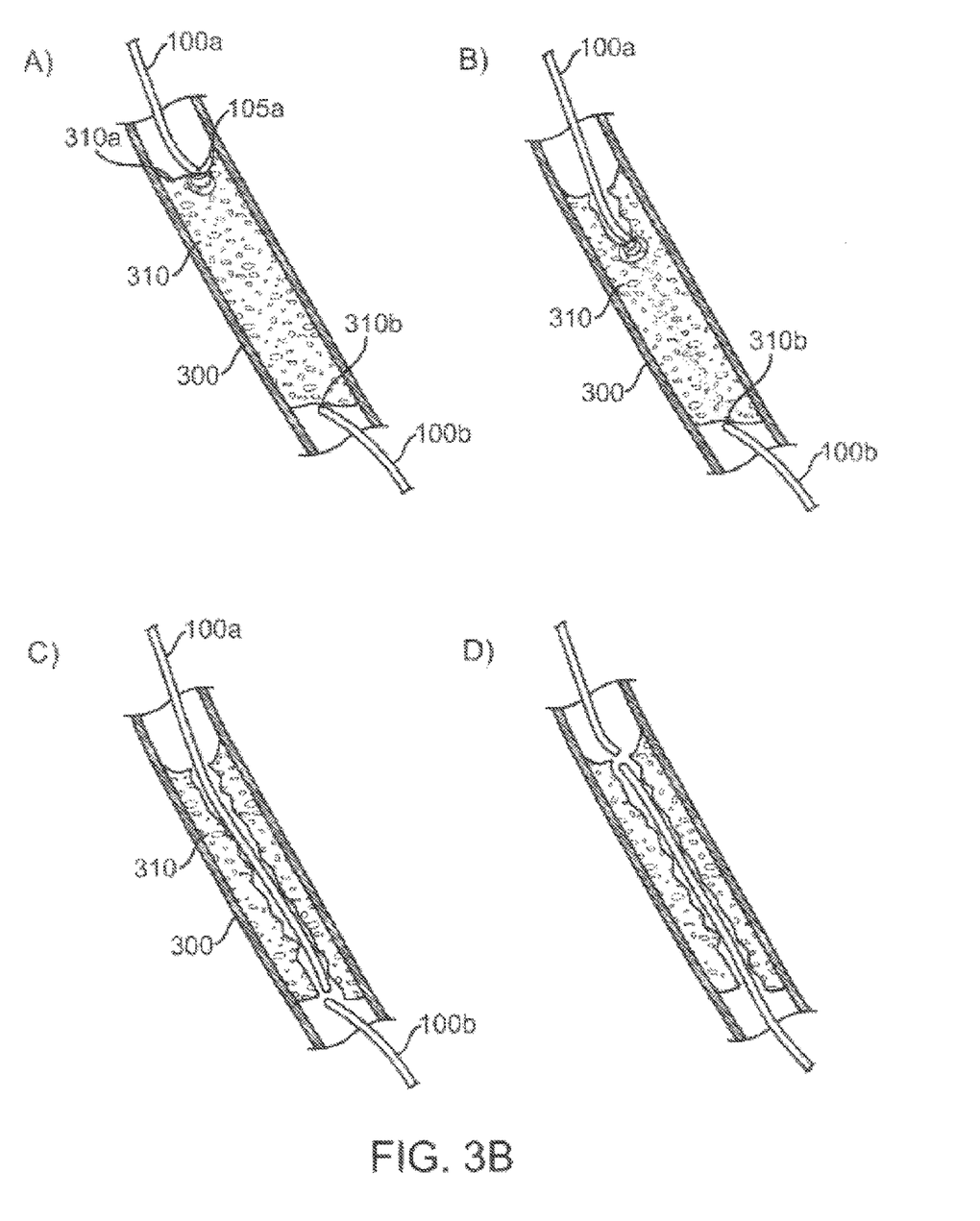

The sequence of the recanalization treatment steps are illustrated in FIGS. 3A and 3B. As shown in diagram A of FIG. 3A, the antegrade guidewire 100a and retrograde guidewire 100b are advanced to the proximal and distal ends 310a and 310b of the occlusion 310, respectively. This can be accomplished using standard angioplasty techniques. As described in the above referenced co-pending U.S. patent application Ser. No. 11/706,041, the retrograde guidewire can be advanced to the distal end of the occlusion 310b using collaterals such as the septals.

Once the user has confirmed that the guidewires 100a and 100b are in contact with the occlusion 310 and are not touching the vessel wall 300, the RF treatment is initiated.

Alternatively, the guidewires are advanced as deep into the occlusion as possible to minimize the distance between the electrodes and, consequently, minimize the length of the ablation zone. Confirmation that the guidewires 100a and 100b are in an appropriate position can be generated by impedance measurements and/or by using any of the standard imaging techniques employed during interventional procedures, such as fluoroscopy or intravascular ultrasound (IVUS), in which transducers are placed on the distal ends of the guidewire. When using tissue impedance measurements, the calcified occlusion 310 generally exhibits significantly higher impedance than the vessel wall 300. If an impedance measurement indicates a low impedance value, it is likely that one or both guidewires are in contact with the vessel wall 300, and appropriate repositioning of the guidewires may be warranted.

Upon initiating the recanalization RF treatment, the occlusion 310 is ablated from the ends 310a and 310b of the occlusion 310 to the interior of the occlusion 310, as shown in FIG. 3A diagram B. The user then slowly and carefully advances one or both guidewires 100a and 100b until a channel or path is created in the occlusion 310, as shown in FIG. 3A diagram C. As shown in FIG. 3A, the antegrade guidewire 100a may be kept stationary and the retrograde guidewire 100b may be advanced through the occlusion 310. Once a channel has been created, the retrograde guidewire 100b may be withdrawn and the antegrade guidewire 100a may be advanced through the occlusion 310, as shown in FIG. 3A diagram D, and standard interventional procedures, such as balloon angioplasty, can be performed. Alternatively, the retrograde guidewire 100b can be kept stationary during the RF treatment and the antegrade guidewire 100a can be advanced through the occlusion 310. This is illustrated in FIG. 3B diagrams A-D.

It is noted that energizing an electrode with radiofrequency energy causes the electrode to generate heat. In general, the amount of such heat is proportional to the amount of radiofrequency energy delivered to the electrode, and inversely proportional to the surface area of the electrode. This is because the smaller the surface area of an electrode, the higher the current density passing through that surface area (for a given total current), which in turn causes the electrode to reach correspondingly higher temperatures. In one embodiment, the system is configured to deliver sufficient radiofrequency energy to an electrode such that radiofrequency sparks are generated.

While it is possible to have the surface areas of the active and return electrodes be of similar size, in a preferred embodiment an active electrode is configured to have a smaller surface area than a return electrode. This allows the active electrode to generate a current density that is sufficiently high to cause radiofrequency sparks crossing over to the return electrode, while at the same time allowing the return electrode surface area to be sufficiently large so as to maximize its contact with the occlusion and attract sparks from the active electrode. Another advantage of such an embodiment is that the return electrode will likely not reach as high temperatures as the active electrode. In one embodiment, the ratio of the return electrode surface area to the active electrode surface area is configured to be in the range of about 50:1 to 2:1, and preferably about 10:1. In one embodiment, the return electrode is configured in a pigtail design to increase surface area contact with the occlusion.

Figure 3C:
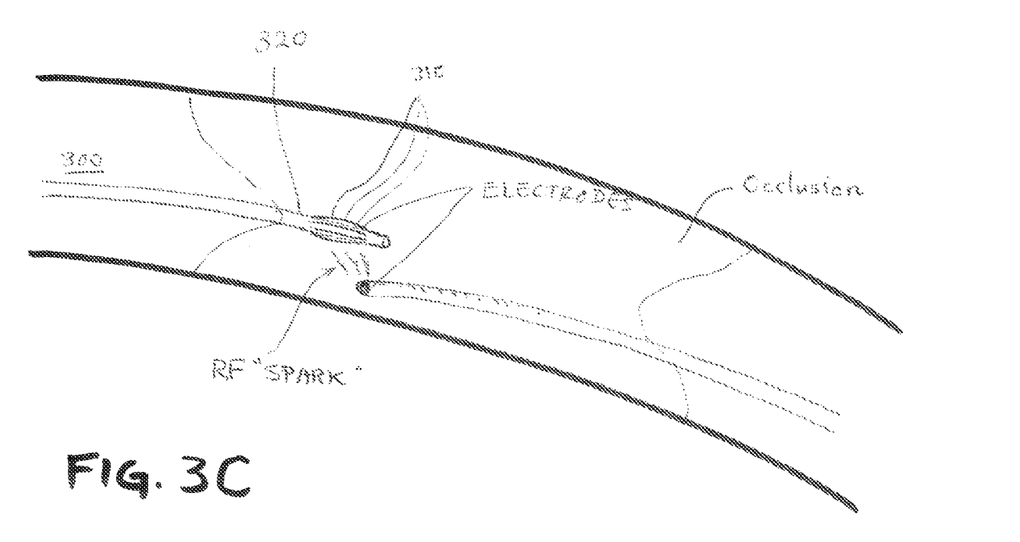
FIGS. 3C-3E show embodiments of electrodes configured to expand outwardly.
Figure 3D:
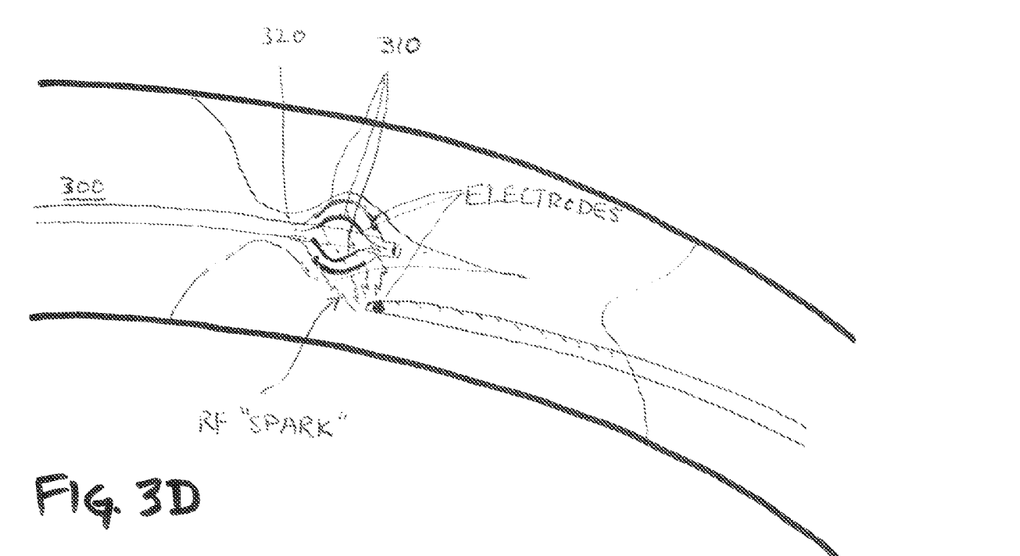

In another embodiment, a plurality of return electrodes may be configured to expand outwardly in order to spread out and increase surface area contact with the occlusion. Such an embodiment is shown in FIG. 3C, where a plurality of ribs 310 are disposed on a distal end 320 of a guidewire 300. The ribs 310 are configured to flare out, as shown in FIG. 3D. In a collapsed state, the ribs 310 are kept under tension, for example by using a restraining sleeve (not shown), by twisting the ribs 310, by exerting a stretching or pulling force on the proximal ends of the ribs 310, etc. The guidewire 300, with the ribs 310 in a collapsed state, is advanced into the occlusion. Upon releasing the tension or pulling back on the restraining sleeve, the ribs 310 flare open.

Figure 3E:
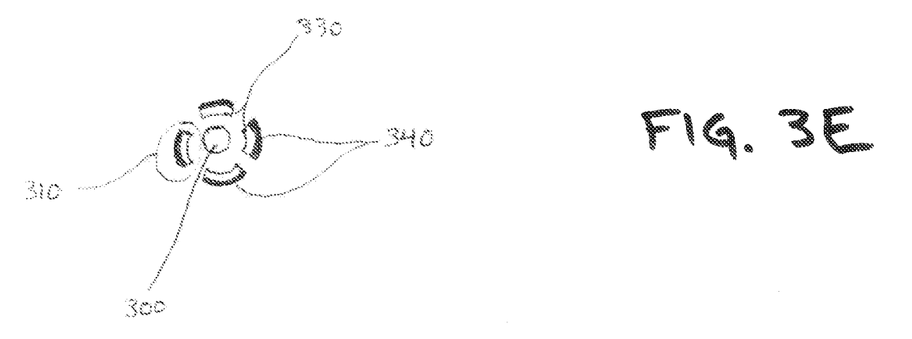

In another embodiment, the ribs 310 comprise electrode areas 330 adjacent to insulator areas 340, as shown in the cross-sectional view of FIG. 3E. In such an embodiment, when the ribs 310 flare out into a basket-like configuration, the insulator areas 340 are on the outside and the electrode areas 330 are on the inside of the basket-like configuration. This configuration advantageously aids in directing radiofrequency energy inside the basket-like configuration while simultaneously providing protection to the surrounding tissue. Alternatively, it is contemplated that in other embodiments the placement of the electrode areas 330 and insulator areas 340 may be varied. In an optional embodiment, a capture device may be configured to comprise one or more electrode areas for use as return electrodes. Examples of capture devices are disclosed in the co-pending U.S. patent application Ser. No. 12/150,111 by the same inventors, which is incorporated herein in its entirety.

Optionally, a centering balloon catheter can be utilized along with the guidewire to center the guidewire within the vessel prior to energizing the system. In such a configuration, it would be advantageous to have a heat resistant tip on the distal end of the balloon catheter.

Figure 4:
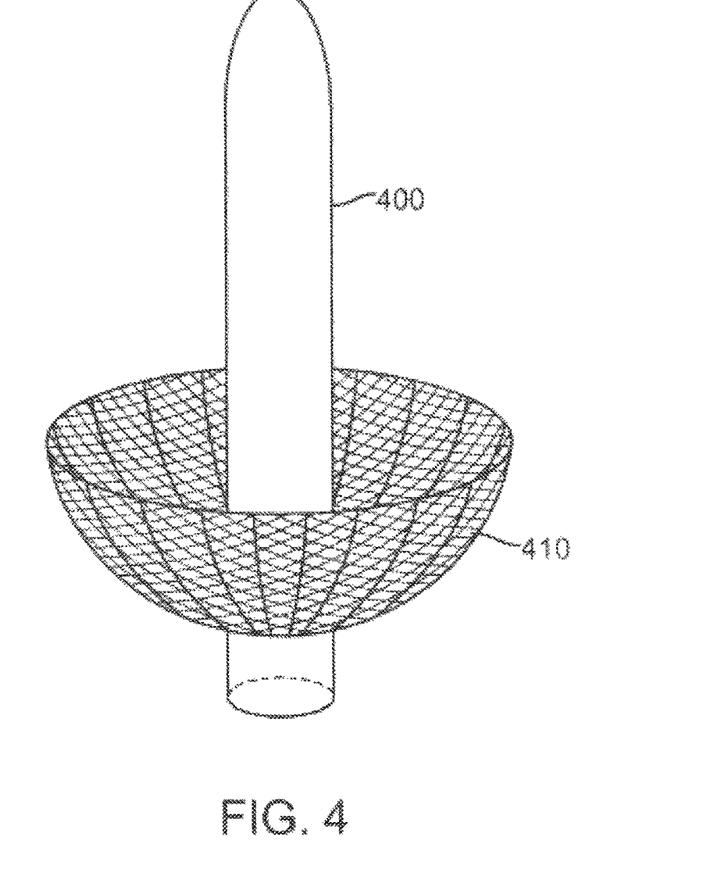
FIG. 4 shows an example embodiment of a longitudinal member comprising an embolic protection mechanism.

Optionally, the catheter comprises a means for removing or withdrawing debris resulting from the RF ablation. For example, a mechanism could be provided to capture and retrieve the debris, or a suction device could be provided to actively remove the debris near the ablation area. Examples of such embolic protection mechanisms are disclosed in the above referenced co-pending U.S. patent application Ser. No. 11/706,041. FIG. 4 shows an example embodiment of a longitudinal member 400 comprising an embolic protection mechanism 410. The embolic protection mechanism 410 comprises a filter, mesh, net, or similar element, for capturing and retrieving ablation debris. As another example, the embolic protection may comprise a balloon for occluding the vessel and preventing the debris from circulating, and for subsequent aspiration of the debris through a longitudinal member. As another example, if a sheath is provided, such sheath may also be configured to be or to include a debris capture and retrieval mechanism or a suction device. In one embodiment, a longitudinal member may be retracted, and the remaining sheath may be used as a capture and retrieval mechanism or a suction device to remove ablation debris. In another embodiment, the longitudinal member comprises an ablating wire housed in the lumen of a dilating catheter. Upon ablation, the ablating wire may be retracted and the dilating catheter may be used to remove the debris. Alternatively, the system comprises a separate catheter to provide suction, or otherwise capture and remove the debris from the ablation site.

Optionally, the device may be coupled to an electrocardiogram (EKG) machine to aid in timing energy emissions. For example, the rate of blood flow through the coronary arteries typically varies during the cardiac cycle. During systole when the heart is contracting, flow through the arteries is generally lower than during diastole. In one embodiment, energy emission is timed during diastole, for example using an algorithm to detect the R-wave of an EKG, and energy emission is timed to occur when flow is highest, thereby maximizing the cooling effect provided by blood flow and consequently minimizing the heat exposure to the vessel. Additionally, coronary artery dimensions can vary during the cardiac cycle and energy emission can similarly be timed to take advantage of this fact.

Optionally, the device may be configured to perform an imaging function, such as intravascular ultrasound or optical coherence tomography (OCT). In one embodiment, this may be accomplished by adding a piezoelectric crystal to a longitudinal member of the device, wherein the piezoelectric crystal may be energized to transmit or receive ultrasonic waves. In another embodiment, an imaging core may be inserted into a longitudinal member of the device (e.g., in the case of a dilating catheter) and operated to transmit and receive ultrasonic waves. In another embodiment, an optical fiber may be used for performing OCT imaging.

Optionally, the device comprises a mechanism for detecting or estimating the distance between the electrodes, and for decreasing the amount of delivered RF energy as the distance between the electrodes decreases, thereby minimizing potential RF injury to the vessel wall.

Figure 5A:
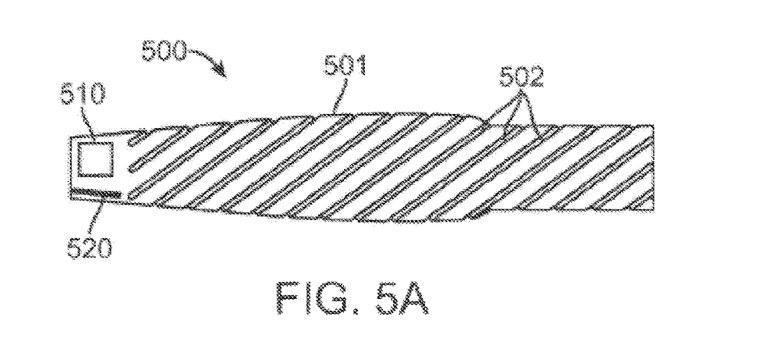
FIGS. 5A-5C show a longitudinal member structurally configured along at least part of the length of the catheter to enable advancement or alignment of the longitudinal member through a narrow diameter blood vessel or occlusion.
Figure 5B:
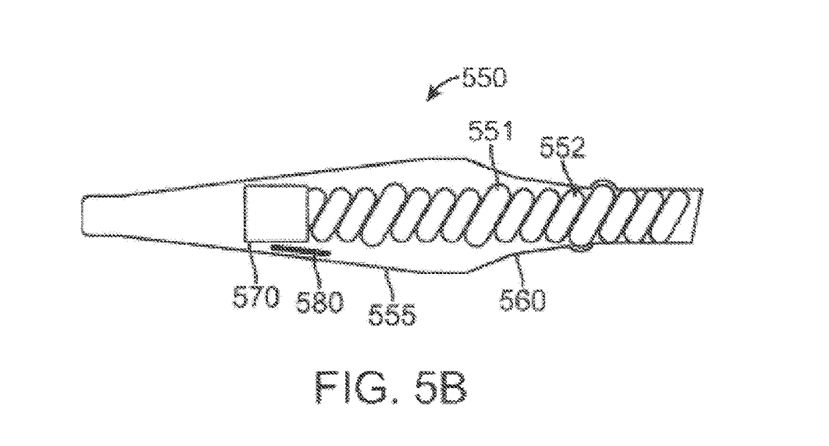
Figure 5C:
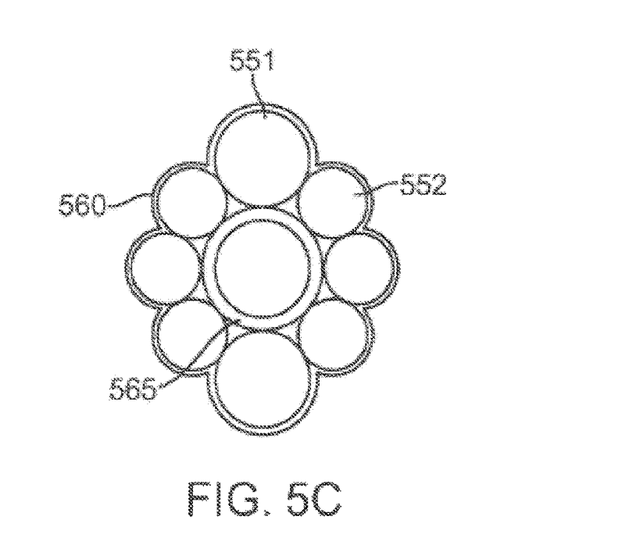

In another embodiment, the device is an ablation catheter comprising a longitudinal member having a distal end, a proximal end, and a guidewire shaft there-between comprising a guidewire lumen. The longitudinal member is a dilating catheter and is structurally configured along at least part of the length of the catheter to enable advancement or alignment of the longitudinal member through a narrow diameter blood vessel or occlusion. Advancement is achieved, for example, by turning or twisting the longitudinal member. FIGS. 5A-5C show such an embodiment of the present invention. For example, as shown in FIG. 5A, the longitudinal member 500 may comprise a helical exterior 501 that advances through the vessel and dilates the vessel as the member is being twisted or rotated. Helical exterior 501 comprises a plurality of grooves 502 carved into the outer body of the longitudinal member 500. The distal tip of longitudinal member 500 optionally comprises a radiopaque marker 510. An electrode 520 is located at or near the distal end of the catheter. Another example is shown in FIG. 5B, the cross section of which is shown in FIG. 5C. The longitudinal member 550 may comprise a plurality of wires 551 and 552 wound around a liner 565. In one embodiment, the wires 551 and 552 comprise at least two different diameters. Longitudinal member 550 optionally terminates at a marker 570. An electrode 580 is located at or near the distal end of the longitudinal member 550. The ablation catheter additionally and optionally comprises conductive wires for transmitting energy between the electrode and an external energy source. Alternatively, the plurality of wires may be configured to act as the electrode or conductive wires. Additionally and optionally, the catheter comprises an insulating sheath 560 which is optionally retractable.

The guidewires and electrodes may be made from any one or more suitable materials as is commonly known in the art. Examples of such suitable materials include stainless steel, Nitinol, Elgiloy, platinum, iridium, tantalum, titanium, cobalt, chromium, tungsten, or any combinations thereof. In one embodiment, one or more of the guidewires may be made of a polymer, with an electrically conductive core for transmitting electrical energy to the respective electrodes.

While the above embodiments refer to the use of RF energy for the purpose of ablation, it should be noted that other energy modalities may be used as well, for example ultrasound energy. In one embodiment, one or more longitudinal members of the recanalization systems of the present invention comprise one or more ultrasound transducers, instead of or in addition to RF electrodes. The ultrasound transducers provide ultrasound energy for ablating an occlusion. In one embodiment, both the antegrade and the retrograde longitudinal members comprise ultrasound transducers and ablate the lesion from an antegrade as well as a retrograde direction. Other energy modalities could include microwave and laser.

It should be noted that the combined antegrade and retrograde energy delivery techniques described above could also be used as an adjunct technique to crossing CTOs in combination with using conventional methods. The technique could be used to sufficiently soften or weaken the occlusion, thereby allowing a guidewire or catheter to cross the occlusion.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A recanalization system, comprising:
a radiofrequency generator;
an antegrade longitudinal member with a proximal end and a distal end, wherein the distal end of the antegrade longitudinal member comprises a first conductive electrode adapted to be positioned at a first location of an occlusion in a blood vessel and the proximal end of the antegrade longitudinal member is configured to be coupled with the radiofrequency generator; and
a retrograde longitudinal member with a proximal end and a distal end the retrograde longitudinal member spaced apart and entirely separate in a non-overlapping arrangement from the antegrade longitudinal member, wherein the distal end of the retrograde longitudinal member comprises a second conductive electrode adapted to be positioned at a second location of the occlusion and the proximal end of the retrograde longitudinal member is configured to be coupled with the radio frequency generator, wherein energy from the radiofrequency generator is emitted from the first conductive electrode to create a channel at least partially through the occlusion from the first location toward the second location.

2. The system of claim 1, wherein the longitudinal members are guidewires or catheters or micro-catheters or dilating catheters.

3. The system of claim 1, wherein the antegrade longitudinal member or the retrograde longitudinal member comprises an insulator.

4. The system of claim 3, wherein the insulator is configured to extend beyond a tip of the first or second conductive electrode, thereby recessing the electrode.

5. The system of claim 3, wherein the insulator is configured to direct radiofrequency energy from one conductive electrode towards the other conductive electrode.

6. The system of claim 1, wherein at least one of the longitudinal members comprises an internal guidewire lumen.

7. The system of claim 1, wherein the longitudinal members have sufficient torsional rigidity and longitudinal flexibility to advance through an occlusion.

8. The system of claim 1, wherein the first or second electrode is mounted on one side of the respective longitudinal member.

9. The system of claim 1, wherein the electrodes are arranged in an array.

10. The system of claim 1, wherein at least one of the longitudinal members comprises a radiopaque marker.

11. The system of claim 1, wherein the longitudinal members are configured to be coupled to the radiofrequency generator via a connector.

12. The system of claim 11, wherein the connector is a torque device.

13. The system of claim 1, wherein at least one of the longitudinal members comprises an embolic protection mechanism for capturing and retrieving debris.

14. The system of claim 13, wherein the embolic protection mechanism is a filter.

15. The system of claim 13, wherein the embolic protection mechanism comprises a balloon.

16. The system of claim 13, wherein the embolic protection mechanism comprises a lumen which allows for aspiration through one of the longitudinal members.

17. The system of claim 1, further comprising an imaging element disposed on the antegrade or retrograde longitudinal member.

18. The system of claim 17, wherein the imaging element is configured to perform ultrasound imaging or optical coherence tomography imaging.

19. The system of claim 1, further comprising an imaging element configured to be placed within a lumen of the longitudinal member.

20. The system of claim 19, wherein the imaging element is configured to perform ultrasound imaging or optical coherence tomography imaging.

21. The system of claim 1, wherein at least one of the longitudinal members is configured to be placed within a catheter or guiding sheath.

22. The system of claim 1, further comprising circuitry for controlling and generating radiofrequency energy.

23. The system of claim 1, further comprising a connection port configured to connect to an EKG to time energy emission.

24. The system of claim 1, wherein the first and second electrodes are configured such that one of the electrodes directs energy towards the other electrode.

25. A recanalization system, comprising:
a radiofrequency generator;
an antegrade longitudinal member with a proximal end and a distal end, wherein the distal end of the antegrade longitudinal member comprises a first conductive electrode adapted to be positioned at a first location of an occlusion in a blood vessel and the proximal end of the antegrade longitudinal member is configured to be coupled with the radiofrequency generator; and
a retrograde longitudinal member with a proximal end and a distal end, the retrograde longitudinal member spaced apart and entirely separate in a non-overlapping arrangement from the antegrade longitudinal member, wherein the distal end of the retrograde longitudinal member comprises a second conductive electrode adapted to be positioned at a second location of the occlusion and the proximal end of the retrograde longitudinal member is configured to be coupled with the radio frequency generator, wherein energy from the radiofrequency generator is emitted from the second conductive electrode to create a channel at least partially through the occlusion from the second location toward the first location.

26. The system of claim 25, wherein the longitudinal members are guidewires or catheters or micro-catheters or dilating catheters.

27. The system of claim 25, wherein the antegrade longitudinal member or the retrograde longitudinal member comprises an insulator.

28. The system of claim 27, wherein the insulator is configured to extend beyond a tip of the first or second conductive electrode, thereby recessing the electrode.

29. The system of claim 27, wherein the insulator is configured to direct radiofrequency energy from one conductive electrode towards the other conductive electrode.

30. The system of claim 25, wherein at least one of the longitudinal members comprises an internal guidewire lumen.

31. The system of claim 25, wherein the longitudinal members have sufficient torsional rigidity and longitudinal flexibility to advance through an occlusion.

32. The system of claim 25, wherein the first or second electrode is mounted on one side of the respective longitudinal member.

33. The system of claim 25, wherein the electrodes are arranged in an array.

34. The system of claim 25, wherein at least one of the longitudinal members comprises a radiopaque marker.

35. The system of claim 25, wherein the longitudinal members are configured to be coupled to the radiofrequency generator via a connector.

36. The system of claim 35, wherein the connector is a torque device.

37. The system of claim 25, wherein at least one of the longitudinal members comprises an embolic protection mechanism for capturing and retrieving debris.

38. The system of claim 37, wherein the embolic protection mechanism comprises a lumen which allows for aspiration through one of the longitudinal members.

39. The system of claim 25, further comprising an imaging element disposed on the antegrade or retrograde longitudinal member.

40. The system of claim 39, wherein the imaging element is configured to perform ultrasound imaging or optical coherence tomography imaging.

41. The system of claim 25, further comprising an imaging element configured to be placed within a lumen of the longitudinal member.

42. The system of claim 41, wherein the imaging element is configured to perform ultrasound imaging or optical coherence tomography imaging.

43. The system of claim 25, wherein at least one of the longitudinal members is configured to be placed within a catheter or guiding sheath.

44. The system of claim 25, further comprising circuitry for controlling and generating radiofrequency energy.

45. The system of claim 25, further comprising a connection port configured to connect to an EKG to time energy emission.

46. The system of claim 25, wherein the first and second electrodes are configured such that one of the electrodes directs energy towards the other electrode.

47. A recanalization system for use with a radiofrequency generator, comprising:
an antegrade longitudinal member with a proximal end and a distal end, the distal end of the antegrade longitudinal member comprises a first conductive electrode adapted to be positioned at a first location of an occlusion in a blood vessel and the proximal end of the antegrade longitudinal member is configured to be coupled with a radiofrequency generator; and a retrograde longitudinal member with a proximal end and a distal end, the retrograde longitudinal member spaced apart and entirely separate in a non-overlapping arrangement from the antegrade longitudinal member, wherein the distal end of the retrograde longitudinal member comprises a second conductive electrode adapted to be positioned at a second location of the occlusion and the proximal end of the retrograde longitudinal member is configured to be coupled with the radio frequency generator, wherein energy from the radiofrequency generator is applied to the occlusion to create a channel at least partially through the occlusion.

* * * * *